US012636516B2

(12) United States Patent
Pomar

(10) Patent No.: US 12,636,516 B2
(45) Date of Patent: May 26, 2026

(54) DEVICE FOR STIMULATING THE MEIBOMIAN GLANDS

(71) Applicants: Morena Gomedi, Bologna (IT); Rodolfo Pomar, Bologna (IT)

(72) Inventor: Rodolfo Pomar, Bologna (IT)

(73) Assignee: ESPANSIONE MARKETING S.P.A., Centergross Funo (IT)

( * ) Notice: Subject to any disclaimer, the term of this patent is extended or adjusted under 35 U.S.C. 154(b) by 383 days.

(21) Appl. No.: 16/606,381

(22) PCT Filed: Apr. 20, 2018

(86) PCT No.: PCT/IB2018/052779
§ 371 (c)(1),
(2) Date: Oct. 18, 2019

(87) PCT Pub. No.: WO2018/193426
PCT Pub. Date: Oct. 25, 2018

(65) Prior Publication Data
US 2021/0187320 A1     Jun. 24, 2021

(30) Foreign Application Priority Data

Apr. 20, 2017     (IT) ......................... 102017000043757

(51) Int. Cl.
*A61N 5/06*          (2006.01)
*A61N 1/40*          (2006.01)

(52) U.S. Cl.
CPC ........... *A61N 5/0625* (2013.01); *A61N 1/403* (2013.01); *A61N 5/0616* (2013.01); *A61N 2005/0626* (2013.01); *A61N 2005/0648* (2013.01); *A61N 2005/0652* (2013.01); *A61N 2005/0659* (2013.01); *A61N 2005/0663* (2013.01)

(58) Field of Classification Search
CPC ...... A61B 18/20–18/28; A61N 5/06–2005/073
USPC ..................................... 606/2–19; 607/88–94
See application file for complete search history.

(56) References Cited

U.S. PATENT DOCUMENTS

| | | | |
|---|---|---|---|
| 8,731,657 B1 | 5/2014 | Shambayati et al. | |
| 2005/0038486 A1 | 2/2005 | Mulholland | |
| 2005/0070977 A1* | 3/2005 | Molina | A61N 5/0616 607/88 |
| 2006/0030908 A1* | 2/2006 | Powell | A61N 5/0616 607/88 |
| 2007/0016269 A1 | 1/2007 | Suzuki | |

(Continued)

FOREIGN PATENT DOCUMENTS

| | | |
|---|---|---|
| DE | 20 2004 010827 U1 | 9/2004 |
| EP | 1 916 016 A1 | 4/2008 |

(Continued)

*Primary Examiner* — Jonathan T Kuo
*Assistant Examiner* — Vynn V Huh
(74) *Attorney, Agent, or Firm* — McGlew and Tuttle, P.C.

(57)     ABSTRACT

The device for stimulating the Meibomian glands comprises a cap (2) and a plurality of light-emitting diodes (3) distributed on the inner surface of said cap (2). The light-emitting diodes (3) are electrically connected to an external control and/or power supply unit (4), provided with a control interface (6). The cap (2) comprises at least one array (30) of light-emitting diodes (3) arranged in areas of the inner surface of the cap (2) designed to face, in use, the eyelids and periocular areas of the user.

20 Claims, 2 Drawing Sheets

(56)     References Cited

U.S. PATENT DOCUMENTS

| | | | |
|---|---|---|---|
| 2009/0124958 A1* | 5/2009 | Li | A61B 18/203 |
| | | | 604/20 |
| 2011/0257467 A1* | 10/2011 | Clegg | A61N 5/0618 |
| | | | 600/27 |
| 2012/0016275 A1* | 1/2012 | Korb | A61N 5/0625 |
| | | | 601/19 |
| 2012/0172951 A1 | 7/2012 | Choi | |
| 2015/0100002 A1 | 4/2015 | Choi | |
| 2015/0127072 A1 | 5/2015 | Pomar | |
| 2015/0134033 A1* | 5/2015 | Tapper | A61N 5/0616 |
| | | | 607/90 |
| 2015/0174425 A1* | 6/2015 | Toyos | A61N 5/0613 |
| | | | 606/127 |
| 2015/0283277 A1 | 10/2015 | Schafer et al. | |
| 2016/0045759 A1* | 2/2016 | Tapper | A61N 5/0616 |
| | | | 607/90 |
| 2016/0056653 A1 | 2/2016 | Tapper et al. | |
| 2017/0014300 A1 | 1/2017 | Dippo et al. | |
| 2017/0312521 A1* | 11/2017 | Franke | A61N 1/36014 |

FOREIGN PATENT DOCUMENTS

| | | | |
|---|---|---|---|
| WO | 2011/141840 A1 | 11/2011 | |
| WO | 2013/003594 A2 | 1/2013 | |
| WO | 2015/178960 A2 | 11/2015 | |
| WO | 2016/070134 A1 | 5/2016 | |

* cited by examiner

DEVICE FOR STIMULATING THE MEIBOMIAN GLANDS

TECHNICAL FIELD

The present invention relates to a device for treating eyelids and periocular areas. More particularly, the invention relates to a device for stimulating the Meibomian glands.

BACKGROUND ART

There are many types of diseases affecting eyelids and causing chronic inflammatory states of the periorbital region, often associated with abnormal tear production. Some examples of such diseases are blepharitis, chalazion, stye and meibomitis.

The alteration of tear production, whether a reduced tear production or an excessive tear evaporation, is the basis of the so-called dry eye syndrome.

The dry eye is an eye disease which consists of a quantitative reduction or a qualitative alteration of the tear film and is characterised by symptoms such as reddening, burning, photophobia, sensation of the presence of a foreign body in the eye and, in the most serious cases, eye pain and blurred vision. In Italy, the dry eye syndrome affects about 26% of the adult population, with a predominance among women after the age of 40 (50%) and those in menopause (90%).

One of the main causes of the dry eye syndrome is the dysfunction of the Meibomian glands that are found inside the eyelids and are responsible for the production of the lipid component of the tear film.

The tear film is in fact formed by three main components: the mucous part which is responsible for the correct distribution of tears on the ocular surface; the aqueous part, i.e., the intermediate and predominant part, produced mainly by the lacrimal glands; and the lipid part, i.e., the superficial part, whose functions are to prevent the tear film from coming out, maintain a good hydration during sleep and regulate the evaporation of the film.

A dysfunction of the Meibomian glands involves an alteration of the lipid layer which causes the appearance of a dry eye with its typical symptoms.

To remedy this problem, different treatments of eyelid disorders, in particular of the dry eye syndrome, have been proposed.

A first solution involves the use of artificial drops aimed at replacing the natural tear film but which, on the other hand, allow only the treatment of the symptoms and not the causes of the disease.

Further solutions act on the causes of the disease and provide, according to a known method, the use of heat, sometimes combined with a mechanical action, which produces a beneficial effect in terms of facilitating the secretion of the lipid component by the Meibomian glands in case of possible obstructions of the glands themselves.

The patent application WO 2013/003594 describes, e.g., an apparatus for treating the obstructions of the Meibomian glands, which provides at least one RF electrode arranged near the surface of the eyelid to selectively transmit radiofrequency radiation towards the glands, more precisely towards the obstructed ducts of the glands, so as to transfer the heat necessary to cause the dissolution or the fluidification of the material that obstructs the ducts. The apparatus also comprises compression means suitable to exert a force on the eyelids or directly on the obstructed ducts to facilitate, in cooperation or as an alternative to the RF electrode, the removal of the occlusion. Such compression means may comprise a needle, a fluid jet such as water or air, a laser.

The patent application WO 2016/070134 describes an apparatus for treating Meibomian gland dysfunctions which comprises a heating element suitable to convey heat towards the eyelid tissue which includes the glands and towards the tissue adjacent to the area where the glands are placed. The apparatus provides a plate suitable to be interposed between the ocular globe and the inner surface of the respective eyelid, connected to a compression member sized to be positioned adjacent to an outer surface of the eyelid so as to exert, together with the plate, a compression force on the eyelid. The plate is associated with the compression member through a pair of arms.

It should however be noted that the treatments which can be carried out using the equipment described above require a high execution accuracy, besides being relatively complex. Furthermore, these solutions are rather invasive and generally require patient anaesthetisation for their implementation.

Therefore, solutions providing for a lower level of invasiveness have been developed. Patent application US 2017/0014300 illustrates, e.g., a mask suitable to be arranged on the user's face by means of a suitable coupling device. The mask comprises a pair of heating members and miniaturized generators of resonant frequency vibrations, both arranged at the eyelids and periorbital region, so as to transfer heat and vibrational energy, respectively, to the eyelids. The heating members are made of resistor elements or metal wires woven into the mask weave and act both as converters of electrical power into thermal energy and as vibration conductors. The coupling device which is interposed between the mask and the skin surface preferably comprises a composition based on a hydrogel contained in a support structure. The mask is provided with a USB port suitable to guarantee the connection to a power supply and control unit by wired means.

A disadvantageous aspect of the mask described is the need to ensure a coupling between the mask and the surface of the skin to be treated by means of a hydrogel layer or an additional material in order to function effectively and safely.

Another known solution is represented by the ocular mask marketed under the name EyeGiene® which provides for a direct application on the eyelid region. In the mask, heating units, developing temporary therapeutic heat, are inserted. However, it has been observed that the beneficial effects of the treatment using this mask do not have an optimal duration.

DISCLOSURE

The task of the present invention is to solve the above-mentioned problems, devising a device that allows to perform the eyelid and periocular area treatment in an optimal manner.

Within this task, it is a further object of the present invention to provide a non-invasive and safe device.

A further object of the invention is to provide a device that does not require a patient preparation to perform the treatment, in particular the need to anaesthetise the patient being avoided.

A further object of the invention is to provide a device for eyelid and periocular area treatment of simple constructional and functional conception, absolutely reliable in functioning, versatile in use and relatively cheap.

The above-mentioned objects are achieved, according to the present invention, by the device for eyelid and periocular area treatment, according to claim 1.

The device for eyelid and periocular area treatment comprises a mask provided with a light-emitting diode array arranged in areas of the inner surface of the same mask suitable to face, in use, the eyelids and the periocular areas of the user, to generate an endogenous heat.

Preferably, said mask has a full eye area to house said light-emitting diode array.

Advantageously, said light-emitting diodes are arranged substantially at the same distance from the user's eyelids.

Preferably said light-emitting diodes are arranged, in use, at a distance from the area to be treated ranging from 5 mm to 200 mm.

Preferably said light-emitting diodes are suitable to emit electromagnetic radiation in wavelengths ranging from 500 nm to 940 nm.

Advantageously, said light-emitting diodes are electrically connected to an external control and/or power supply unit.

Advantageously, said external control and/or power supply unit is equipped with a control interface.

Advantageously, said interface consists of a touch screen or a screen associated with suitable control buttons.

Advantageously, said external control and/or power supply unit comprises a computer and a computer readable memory.

Advantageously, said memory comprises instructions which, when executed by said computer, cause said computer to automatically select a plurality of said light-emitting diodes and automatically set the power and/or emission duration to cause the stimulation of the Meibomian glands of the user.

Advantageously, said mask is associated with supporting means suitable to keep the same mask, in use, in a predetermined position in front of the user's face.

Preferably, said mask is made of a laminar body of polymeric material.

Preferably said laminar body of the mask comprises an outer layer and an inner layer which is suitable to house said light-emitting diodes in the thickness, said outer layer and said inner layer being made firmly integral with each other.

Preferably, said inner layer of the laminar body of the mask has a pair of openings at the eyelids and periocular areas of the user, so as to house respective arrays of said light-emitting diodes.

Said openings of the inner layer of the laminar body are closed at the bottom by said outer layer of the laminar body.

Preferably said light-emitting diodes are connected to respective electrical power supply circuits incorporated between said outer layer and said inner layer of the laminar body of the mask.

Also, an object of the invention is a computer program comprising instructions that cause the device to perform the steps of receiving from the user, by means of said control interface, data related to a treatment to be performed; memorizing said data; on the basis of said acquired and stored data, automatically selecting a plurality of said light-emitting diodes and automatically setting their power and/or emission duration; actuating said plurality of said light-emitting diodes for the set emission duration, to cause stimulation of the Meibomian glands of the user.

Also, an object of the invention is a computer readable memory, wherein the above-mentioned computer program is loaded.

DESCRIPTION OF DRAWINGS

The details of the invention will become more evident from the detailed description of a preferred embodiment of the device for eyelid and periocular area treatment according to the invention, illustrated by way of example in the accompanying drawings, wherein.

BEST MODE

Figure 3:
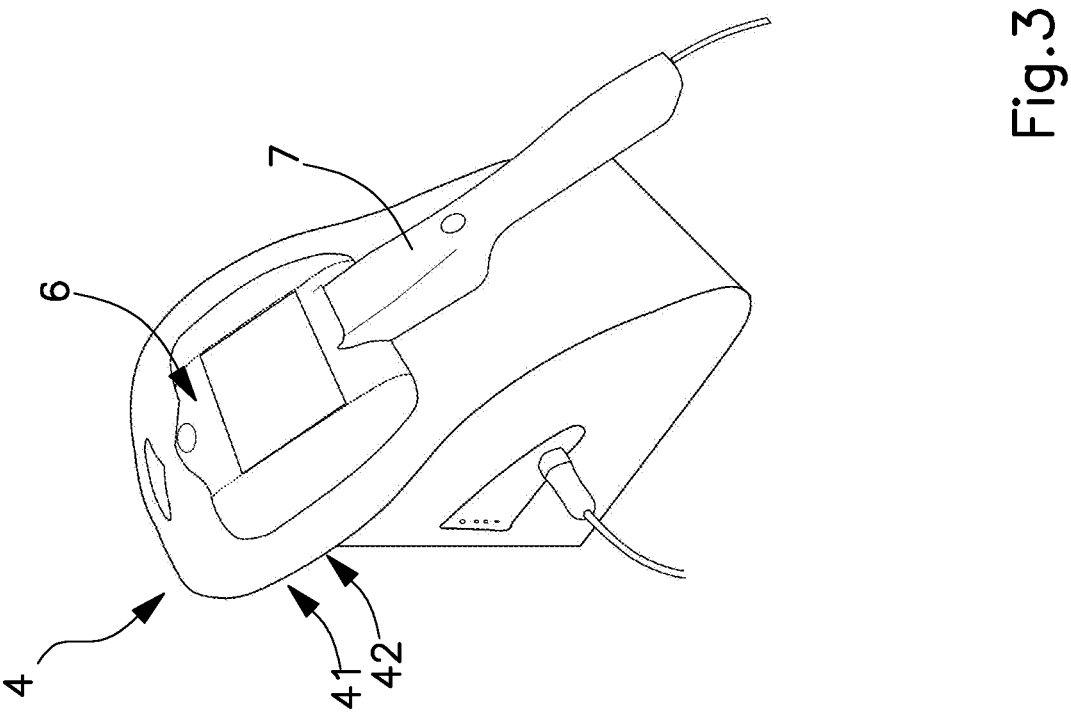
FIG. 3 shows a control and/or power supply unit suitable to be associated with the present device.
Figure 1:
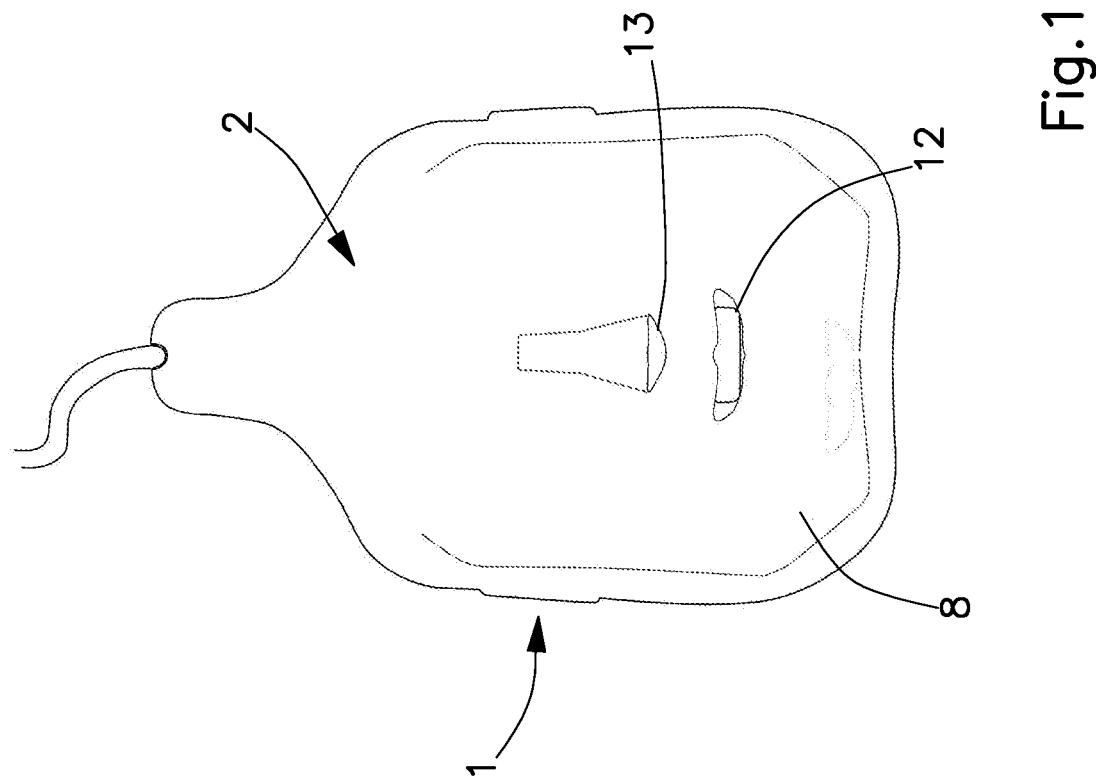
FIG. 1 shows a front view of the device according to the present invention.
Figure 2:
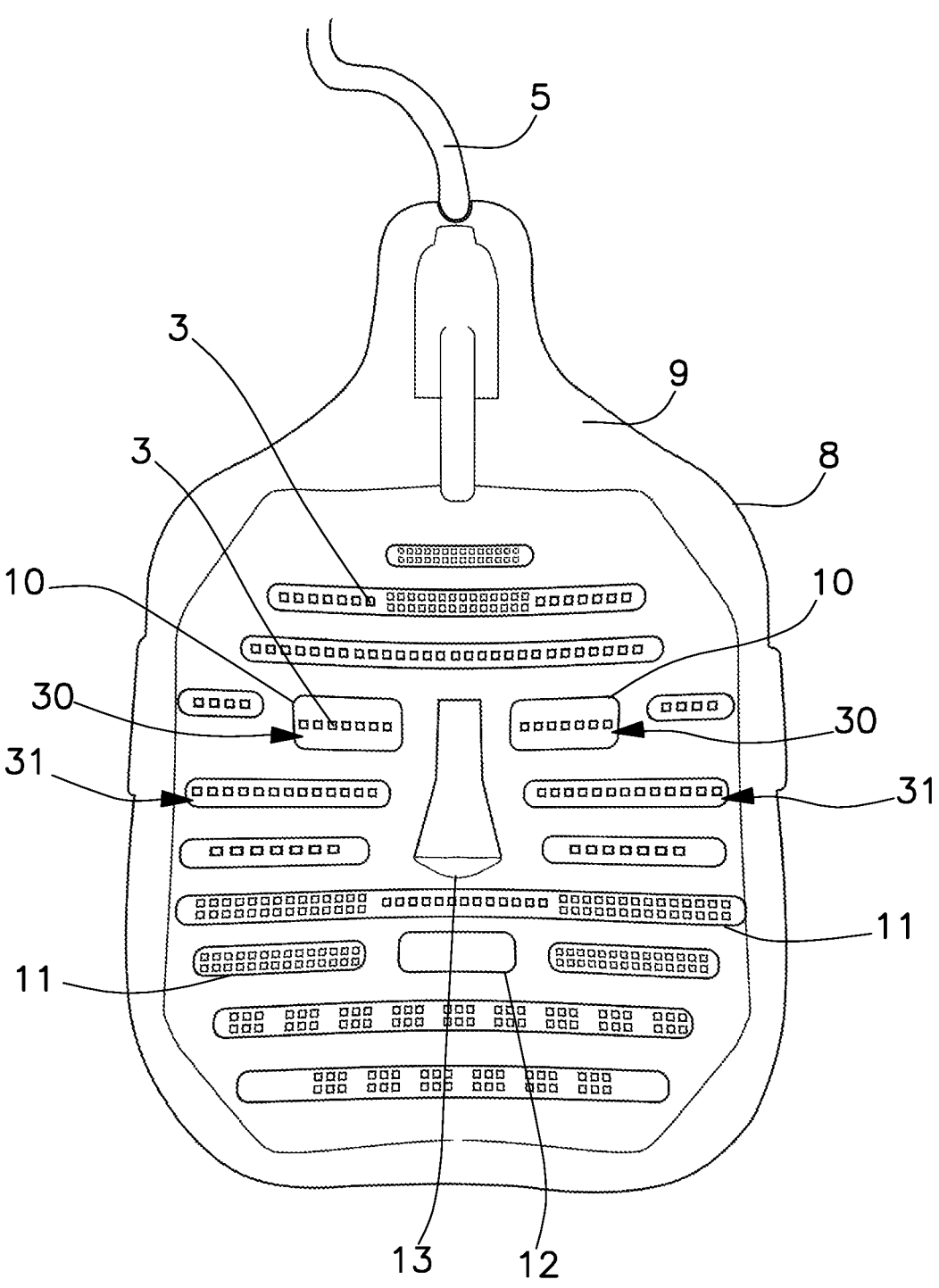
FIG. 2 shows a view of the inner surface of the same device, facing, in use, the user's face.

With particular reference to these figures, the device for eyelid and periocular area treatment according to the invention is referred as a whole by reference numeral 1.

The device 1 is made of a cap 2 preferably having the shape of an anthropomorphic mask. Such mask 2 is composed of a laminar body incorporating a plurality of light sources 3 of the light-emitting diodes type, for the sake of simplicity usually indicated by the acronym LED.

The mask 2 is associated with appropriate supporting means, not seen in the figures, suitable to maintain, in use, the same mask in a predetermined position in front of the user's face.

The LEDs 3 are connected to appropriate electrical circuits, known per se and, therefore, not shown, which allow to manage the power supply and the correct operation of the diodes. The LED circuits 3 are electrically connected to a control and/or power supply unit 4 of the device. The control and/or power supply unit 4 is arranged externally with respect to the mask 2 and is connected thereto by means of an appropriate connecting cable 5.

The control unit 4 comprises a control interface 6 suitable to allow an easy setting of the parameters characterising the treatment, such as, e.g., the duration of the treatment or the selection of the diodes to be activated according to the type of desired treatment, as will be better explained further below. The interface 6 can be made of a touch screen or a screen associated with suitable control buttons.

Alternatively, it is possible to provide that the control interface which sets the treatment parameters is integrated within the mask 2.

According to an embodiment of the invention, the control unit 4 is provided with a handpiece 7 housing appropriate neuronal stimulation means, suitable to induce muscle contractions which increase the action of the LEDs. Such neuronal stimulation means can be constituted, e.g., by RF, pulsed light, heat emitters and the like.

For example, such stimulation means can be constituted by a polychromatic light which, when applied on the periorbital and cheekbone areas, thanks to thermal impulses stimulates the contraction of the Meibomian glands, increasing the lipid flow and reducing tear evaporation.

Thanks to the synergy between the LEDs 3 and the stimulation means housed in the handpiece 7, the Meibomian glands resume the production of the lipids necessary for the functionality of the eye. The tests performed have shown that after a few hours of treatment, an improvement in the functionality of the Meibomian glands can be appreciated.

In a different embodiment, it is possible to provide that the LED circuits 3 are connected to a controller associated with the mask 2, suitable to manage the operation of the LEDs 3, and that the outer unit 4 is used only to power the LEDs 3.

The laminar body of the mask 2 has a thickness suitable for the insertion of the LEDs 3 and the related circuits. The LEDs are distributed on the inner surface of the mask 2, facing, in use, the user's face. In particular, the LEDs 3 are distributed so as to create at least one array 30 in the areas of the inner surface of the mask 2 which face, in use, the eyelids and the periocular areas of the user.

The laminar body of the mask 2 is preferably made of a polymeric material. Alternatively, it is possible to provide that the mask 2 is made of other suitable materials such as leather, hide, fabric and/or paper derivatives.

The mask 2 has a full eye area so as to house the above-mentioned array 30 of LEDs 3. More specifically, for each eye, an area suitable to house a respective array 30 of LEDs 3 is provided in the mask 2. In this way the arrays 30 of LEDs 3 can be used for the treatment of diseases affecting the eyelids and the periocular areas. More specifically, the arrays 30 are sized so as to irradiate both the upper and the lower eyelids of the user as well as the periocular areas.

The mask 2 may also have, in other areas, e.g., at different parts of the face such as the forehead, the cheeks and/or the chin, further arrays 31 of LEDs 3 suitable to be used for appropriate cosmetic and/or therapeutic treatments on the skin.

According to a preferred embodiment, the laminar body of the mask 2 consists of a first outer layer 8 and a second inner layer 9, made integral with each other.

The LEDs 3 and their related circuits are housed in the thickness of the second inner layer 9. The second inner layer 9 has a pair of openings 10 at the eye area so as to expose the arrays 30 of the LEDs 3 towards the eyelids and the periocular areas.

Preferably, the openings 10 have an oval shape so as to define respective full areas having a shape suitable to irradiate, through the LEDs 3 of the arrays 30, the entire surface of the upper and lower eyelids together with the periocular areas.

On the second inner layer 9 there is also a set of further openings 10, preferably shaped in strips, suitable to house the further arrays 31 of LEDs 3. The strips have different lengths depending on the region of the mask in which they are made and are arranged sequentially one after the other along a longitudinal direction of the mask.

Preferably, at the mouth and nose, openings 12, 13 passing through the first layer 8 and the second layer 9 are realized on the mask in order to allow a suitable air circulation to the user and thus increase his/her well-being during the treatment.

LEDs 3 are distributed on the mask 2 substantially at the same distance from the eyelids of the user, to generate an endogenous heat. The distance is appropriately calculated based on the intensity and frequency features of the light beam emitted by the LEDs 3.

Preferably the LEDs 3 are arranged, in use, at a distance from the area to be treated ranging from 5 mm to 200 mm.

The LEDs 3 distributed on the mask 2 can exhibit different features, e.g., they can be suitable for the emission of a red light beam to stimulate the production of collagen, or a blue beam to counteract the bacterial acne or a yellow beam to stimulate the lymphatic system and the nervous system, or even an infrared beam. Preferably, LEDs 3 having different features are combined in the same mask 2 to perform mixed treatments.

Preferably, the LEDs 3 are suitable to emit electromagnetic radiation having a wavelength ranging between 500 nm and 940 nm.

It is possible to provide that the surfaces of the LEDs 3 facing the skin to be treated are covered by a special filter suitable to eliminate possible potentially dangerous frequencies present in the emission spectrum of the LEDs 3.

The operation of the device for treating the skin, in particular the eyelids and the periocular areas, is easily understandable from the above description.

First of all, the mask 2 is arranged in front of the user's face by means of suitable supporting means.

The operator sets the type of treatment to be performed through the interface 6 of the control and/or power supply unit 4, e.g., the stimulation of the eyelids. The operator then enters the parameters suitable for this type of treatment, e.g. its duration and wavelength.

Once the treatment parameters have been set, the operator turns on the device and the user is subjected to treatment for a predetermined time interval.

In particular, to perform the treatment of diseases affecting the eyelids and the periocular regions, the LEDs 3 of the arrays 30 arranged at the area of the eyes are activated. The arrays 30 irradiate the regions to be treated, generating an endogenous heat in the eyelids. In fact, the emitted electromagnetic radiations interact with predetermined organelles of the cells of the irradiated tissues, triggering the production of ATP (adenosine triphosphate) which is associated with the production of thermal energy. In particular, the light beams emitted by the LEDs 3 stimulate the production of endogenous heat which has a beneficial effect on the Meibomian glands dysfunctions, in particular on possible obstructions since it allows to fluidize the material that occludes the glands.

In the event that a mixed treatment is performed, e.g. a treatment of the eye area together with a cosmetic or therapeutic treatment of other facial areas, the array 30, 31 of LED 3 arranged at the regions concerned are activated.

The treatment performed by means of LEDs 3 can be associated with the action of appropriate neuronal stimulators, such as RF, pulsed light, heat emitters and the like, to induce muscular contractions that increase the action of the same LEDs. Such second treatment is suitably performed by means of the handpiece 7 of the control and/or power supply unit 4.

The device according to the present invention achieves the object of allowing a non-invasive and safe treatment of the skin, in particular of the eyelids and periocular areas.

In fact, it must be noted that the mask is arranged in front of the user's face, at an appropriate distance, therefore the user is irradiated by the light beam of the LEDs without the need to directly contact the user's skin with the energy source. It should be emphasized that the heat used for the treatment is of the endogenous type, therefore no thermal energy is applied from the outside on the user's skin, eliminating any risk associated with heat exposure.

The control unit allows to set the parameters of the treatment to be performed according to the needs and features of the user with an increased safety for the user.

An important aspect to emphasize is also the fact that it is not required a particular preparation of the user for the treatment and, therefore, the operating times are optimized besides the fact that the risks associated with preparations sometimes adopted, such as anaesthetics, are greatly reduced.

The specific conformation of the device, in particular of the full areas of the cap housing the diodes, allows to treat both the upper and the lower eyelids as well as the periocular areas exhaustively irradiating all the areas of potential interest for most of the eyelid diseases.

Furthermore, the device is structurally simple and is not complex to manage, therefore a highly specialised training of the operator is not required.

The device for treating the skin, described by way of example, is susceptible of several modifications and variations depending on the different requirements. In particular, the cap may be made in a manner different from what illustrated above, e.g., with limited dimensions so as to substantially cover only the eyelids and the periocular areas.

According to a preferred embodiment of the device, the external control and/or power supply unit 4 comprise a computer 41 and a computer readable memory 42.

The memory 42 comprises instructions which, when executed by the computer 41, cause the computer 41 to automatically select a plurality of said light-emitting diodes 3 and automatically set the power and/or emission duration to cause the stimulation of the Meibomian glands of the user.

In particular, the memory 42 can comprise instructions which, when executed by the computer 41, cause the computer 41, according to data set by the user through the control interface 6, to automatically select a plurality of said light-emitting diodes 3 and automatically set the power and/or emission duration to cause the stimulation of the Meibomian glands of the user.

In the practical embodiment of the invention, the materials used, as well as shape and dimensions, may be any according to requirements.

Where the technical features mentioned in any of the claims are followed by reference numerals, these reference numerals are included to improve the comprehension of the claims only, and consequently they have no limiting effect on the object of each element identified by way of example by these reference numerals.

The invention claimed is:

1. A device for stimulating Meibomian glands of a user, the device comprising:

a cap configured to be arranged in a position in front of a face of said user, said cap comprising a longitudinal axis;

a plurality of light-emitting diodes distributed on an inner surface of said cap;

an external control and/or power supply unit electrically connected to said plurality of light-emitting diodes and said external control and/or power supply unit being provided with a control interface, said plurality of light-emitting diodes comprising at least one array of light-emitting diodes arranged in areas of said inner surface of said cap configured to face, in use, eyelids and periocular areas of said user, said plurality of light-emitting diodes being arranged substantially at a same distance from said eyelids of said user, to generate an endogenous heat, said control unit and/or power supply unit being provided with a handpiece housing a neuronal stimulation means, for increasing the action of said plurality of light-emitting diodes, wherein at least one array of said plurality of light-emitting diodes is configured to be arranged opposite each of said eyelids, said at least one array of light-emitting diodes comprising a single strip of said light-emitting diodes arranged along a direction transverse of said longitudinal axis of said cap, said neuronal stimulation means comprising radio frequency, pulsed light or heat emitters, wherein said radio frequency, pulsed light or heat emitters are configured to be controlled via said external control and/or power supply unit such that one of radio frequency, pulsed light and heat from said radio frequency, pulsed light or heat emitters induce muscular contractions to increase the action of the light-emitting diodes, wherein said plurality of light-emitting diodes are arranged, in use, at a distance from an area to be treated ranging from more than 5 mm to 200 mm, wherein each of said light-emitting diodes in said single strip is configured to be arranged at a same distance from one of said eyelids of said user in said range greater than 5 mm and equal to or less than 200 mm, wherein said cap is substantially shaped in a form of a mask, said mask having a full eye area to house said at least one array of said plurality of light-emitting diodes, wherein said mask has further full areas at different areas of said face housing further arrays of said plurality of light-emitting diodes configured to be used to perform cosmetic and/or therapeutic treatments on skin, wherein said further arrays are arranged sequentially one after the other along said longitudinal axis of the mask, parallel to said at least one array of said plurality of light-emitting diodes configured to be arranged opposite each of said eyelids, wherein said mask comprises a first outer layer and a second inner layer, superimposed on said first outer layer, said second inner layer being configured to house said plurality of light-emitting diodes in a thickness of said second inner layer, said first outer layer being integrally connected to said second inner layer, said light-emitting diodes and circuits associated with said light-emitting diodes being housed in said second inner layer, wherein said second inner layer has a plurality of openings in a shape of a strip to provide a plurality of strips, each of said strips being configured to house one of said further arrays of said light-emitting diodes, one of said strips extending between a mouth and a nose of said mask, wherein said one of said strips extends perpendicular to the longitudinal axis from one side of the longitudinal axis to another side of the longitudinal axis.

2. A device according to claim 1, wherein said external control and/or power supply unit comprises:

a computer;

a computer readable memory comprising instructions which, when executed by said computer, cause said computer to automatically select a plurality of said plurality of light-emitting diodes and automatically set a power and/or emission duration to cause stimulation of said Meibomian glands of said user.

3. A device according to claim 2, wherein said computer readable memory comprises further instructions which, when executed by said computer, cause said computer, according to data set by said user through said control interface, to automatically select a plurality of said plurality of light-emitting diodes and automatically set said power and/or emission duration to cause said stimulation of said Meibomian glands of said user.

4. A device according to claim 1, wherein said at least one array of said plurality of light-emitting diodes configured to be arranged opposite one of said eyelids and said at least one array of said plurality of light-emitting diodes configured to be arranged opposite another one of said eyelids are symmetrical with respect to said longitudinal axis of said cap.

5. A device according to claim 4, wherein said mask has, at said mouth and said nose, respective openings passing through said first outer layer and said second inner layer so as to allow air circulation to said user and increase well-being of said user during treatment, said second inner layer having openings in a shape of a strip, each strip extending perpendicular to said longitudinal axis, each strip being configured to house one of said further arrays of said light-emitting diodes, another strip extending at a position below said mouth from one side of said longitudinal axis to said another side of said longitudinal axis, yet another strip extending above said nose of said mask from one side of said longitudinal axis to said another side of said longitudinal axis.

6. A device according to claim 1, wherein said cap is made of polymeric material, said plurality of light-emitting diodes in said single array being arranged in a linear direction.

7. A device according to claim 1, wherein said plurality of light-emitting diodes are configured to emit electromagnetic radiation in wavelengths ranging from 500 nm to 940 nm, said plurality of light-emitting diodes in said single array form a linear arrangement of light-emitting diodes.

8. A device according to claim 1, wherein said second inner layer has at least one pair of openings at eyes of said user so as to expose arrays of said plurality of light-emitting diodes towards said eyelids and periocular areas, said second inner layer comprising a further pair of openings at said eye area configured to house further arrays of said light-emitting diodes, each of said further openings being in a shape of a strip to provide a plurality of strips, said strips having different lengths based on a region of said mask in which said strips are made and said strips being arranged sequentially one after another along a longitudinal direction of said mask.

9. A device according to claim 8, wherein said mask has, at said mouth and said nose, respective openings passing through said first outer layer and said second inner layer so as to allow air circulation to said user and increase well-being of said user during treatment.

10. A device according to claim 1, wherein said mask has, at said mouth and said nose, respective openings passing through said first outer layer and said second inner layer so as to allow air circulation to said user and increase well-being of said user during treatment.

11. A device according to claim 1, wherein said different areas of said face comprise one or more of a chin, a forehead and cheeks of said user.

12. A device according to claim 1, wherein said neuronal stimulation means is configured to apply said one of said radio frequency, said pulsed light and said heat on periorbital and cheekbone areas of the user, wherein said endogenous heat increases a temperature of said eyelids of said user.

13. A device according to claim 1, wherein the mask comprises a mask body, the second inner layer having a pair of openings at an eye area configured to expose arrays of the light-emitting diodes towards the eyelids and periocular areas, the second inner layer further comprising a set of further openings configured to house further arrays of the light-emitting diodes, the further openings being shaped in strips, the strips having different lengths based on a region of the mask in which the strips are made and the strips being arranged sequentially one after the other along a longitudinal direction of the mask body.

14. A device according to claim 1, wherein said one of said strips comprises a first row of said light-emitting diodes, a second row of said light-emitting diodes, a third row of said light-emitting diodes, a fourth row of said light-emitting diodes and a fifth row of said light-emitting diodes, said third row of said light-emitting diodes being located between said first row of said light-emitting diodes, said second row of said light-emitting diodes, said fourth row of said light-emitting diodes and said fifth row of said light-emitting diodes, said first row of said light-emitting diodes and said second row of said light-emitting diodes being located opposite said fourth row of said light-emitting diodes and said fifth row of said light-emitting diodes in a direction perpendicular to said longitudinal axis, said first row of said light-emitting diodes being located opposite said second row of said light-emitting diodes in a direction parallel to said longitudinal axis, said fourth row of said light-emitting diodes being located opposite said fifth row of said light-emitting diodes in said direction parallel to said longitudinal axis.

15. A process comprising:
providing a non-transitory computer-readable storage medium storing a computer program comprising instructions that cause a device according to claim 1 to perform the following steps:
receiving from said user, through said control interface, data related to a treatment to be performed;
storing said data;
automatically selecting a plurality of said plurality of light-emitting diodes and automatically setting a power and/or an emission duration based on said data;
actuating said plurality of said plurality of light-emitting diodes for said emission duration, to cause stimulation of said Meibomian glands of said user;
activating a neuronal stimulation means to increase the action of said plurality of light-emitting diodes, said neuronal stimulation means comprising radio frequency, pulsed light or heat emitters.

16. A process according to claim 15, wherein radio frequency, pulsed light or heat emitted via said radio frequency, pulsed light or heat emitters induces muscular contractions to increase the action of the light-emitting diodes.

17. A process according to claim 15, wherein actuation of said plurality of light-emitting diodes is associated with activation of said radio frequency, pulsed light or heat emitters such that one of radio frequency, pulsed light and heat from said radio frequency, pulsed light or heat emitters induce muscular contractions to increase the action of the light-emitting diodes.

18. A non-transitory computer readable memory, wherein a computer program is loaded on the non-transitory computer readable memory, the computer program comprising instructions that cause a device according to claim 1 to perform the following steps:
receiving from said user, through said control interface, data related to a treatment to be performed;
storing said data;
automatically selecting a plurality of said plurality of light-emitting diodes and automatically setting a power and/or an emission duration based on said data;
actuating said plurality of said plurality of light-emitting diodes for said emission duration, to cause stimulation of said Meibomian glands of said user;
activating a neuronal stimulation means to increase the action of said plurality of light-emitting diodes, said neuronal stimulation means comprising radio frequency, pulsed light or heat emitters.

19. A non-transitory computer readable memory according to claim 18, wherein said radio frequency, pulsed light or heat emitters are activated to emit radio frequency, pulsed light or heat such that muscular contractions are induced to increase the action of the light-emitting diodes.

20. A non-transitory computer readable memory according to claim 18, wherein said plurality of light-emitting diodes and said radio frequency, pulsed light or heat emitters are associated with one another such that one of radio frequency, pulsed light and heat from said radio frequency, pulsed light or heat emitters induce muscular contractions to increase the action of the light-emitting diodes.

* * * * *